United States Patent [19]

Eggers

[11] Patent Number: 5,392,319
[45] Date of Patent: Feb. 21, 1995

[54] ACCELERATOR-BASED NEUTRON IRRADIATION

[75] Inventor: Philip E. Eggers, Dublin, Ohio

[73] Assignee: Eggers & Associates, Inc., Dublin, Ohio

[21] Appl. No.: 994,942

[22] Filed: Dec. 22, 1992

[51] Int. Cl.$^6$ ............................................... G21G 1/10
[52] U.S. Cl. ..................................... 376/194; 376/151
[58] Field of Search ................ 376/115, 190, 191, 194, 376/196, 199, 151; 250/282, 390.1

[56] References Cited

U.S. PATENT DOCUMENTS

| | | | |
|---|---|---|---|
| 3,733,490 | 5/1973 | Roche | 376/151 |
| 4,090,085 | 5/1978 | Cranberg | 376/115 |
| 4,112,306 | 9/1978 | Nunan | 376/112 |
| 4,192,998 | 3/1980 | Azam | 376/190 |
| 4,360,495 | 11/1982 | Bauer | 376/194 |
| 4,582,667 | 4/1986 | Bauer | 376/194 |
| 4,599,515 | 7/1986 | Whittemore | 376/110 |
| 4,666,651 | 5/1987 | Barjon et al. | 376/151 |

OTHER PUBLICATIONS

"Practical Problems of the Past in the Use of Boron–Slow Neutron Capture Therapy in the Treatment of Glioblastoma Multiforme", Sweet, Massachusetts General Hospital, (no date).
"A Neutronic Study of An accelerator Based Neutron Irradiation Facility For Boron Neutron Capture Therapy", Wang et al., Nuclear Technology, Jan. 1989, pp. 93–107.
"An Experimental Study of the Moderator Assembly for a Low Energy Proton Accelerator Neutron Irradiation Facility for BNCT", Wang et al., (1990), pp. 270–280.
Biological Effects and Therapeutic Possiblities of Nuetrons Locher, American Journal of Roentgenology vol. 36, No. 1 (1936).
Boron Uptate by Human Brain Tumors and Quality Control of Boron Compounds, Boron–Neutron Capture Therapy of Tumors, Hatanaka, Nishimura Co., Ltd. p. 77 (1986).
Hatanaka, "Clinical Experience of Boron–Neutron Capture Therapy for Gliomas-A Comparison with Conventional Chemo–Immuno–Radiotherapy" Boron–Neotron Capture Therapy; Nishimura Co., Ltd. p. 349 (1986).
Joel, et al. "Phamakinetics and Tissue Distribution of the Sulfhydryl boranes (Monomer and Dimer) in Glioma-Bearing Rats", Strahlenther, Onkol., vol. 165, p. 167 (1989).
Codere, et al. "Selective Delivery of Boron by the Melanin Precursor Analogue, p-Boron phenylalanine to Tumors other than Melanoma" Cancer Research 50, p. 138 (Jan. 1990).
"A Study of Low Energy Proton Accelerators for Neutron Capture Therapy" NASA Lewis Research Center Dynamitron, (Oct. 1985).
Conceptual Design of RFO Accelerator-Based Neutron Source for Boron Neutron-Capture Therapy, Wangler, et al. (no date).

*Primary Examiner*—Daniel D. Wasil
*Attorney, Agent, or Firm*—Mueller and Smith

[57] ABSTRACT

System and apparatus for producing neutron beams having an energy spectrum and intensity suitable for use in neutron capture therapy. The apparatus employs a rotating carriage which supports an annular target support region carrying a target material such as lithium metal. The carriage rotatably positions the target material before the pathway of charged particles generated from an accelerator course of ions. To cool the assemblage, the carriage is formed having an internally disposed chamber within which a coolant is directed from an external source. Because of the centrifugal forces imposed upon this internally-disposed coolant, it is forced to a heat exchange position adjacent the target region. The assemblage of carriage and accelerator are retained within a containment chamber under vacuum. Surrounding these components at the vicinity of the charged particle or ion pathway is a containment and moderator assembly serving to modulate the energies of generated neutrons while reflecting desired neutrons into a neutron output stream and absorbing thermal neutrons and undesired gamma radiation.

15 Claims, 9 Drawing Sheets

ACCELERATOR-BASED NEUTRON IRRADIATION

The present invention relates to the production of neutron beams having an energy spectrum and intensity or beam current suitable for use in neutron capture therapy for treatment of cancer, and, more generally, the selective destruction of tissue or cells in close proximity to a neutron capture agent. As such, the invention is particularly adapted for utilization in a hospital environment for routine treatment of patients suffering from cancer and other similar diseases where tissue or cells need to be selectively destroyed. The system disclosed also is suitable for the production of neutron beams having energy spectra suitable for, but not limited to, neutron radiography and neutron activation analysis.

BACKGROUND OF THE INVENTION

The concept of neutron capture therapy was first proposed by Locher in 1936 as a means for treating cancer. In this therapy, a capture agent with a large neutron cross section is transported to and selectively accumulated in tumor cells. Upon irradiation by low-energy neutrons, the capture agent localized in the tumor "absorbs" the neutrons and emits highly ionizing and localized radiation which is lethal to cells. See in this regard:

Locher, G. I. "Biological Effects of Therapeutic Possibilities of Neutrons", American Journal of Roentgenology, Vol. 36, No. 1 (1936).

Locher's concept for neutron capture therapy has progressed over the past 50 years to the identification of suitable (1) capture agents, (2) pharmaceuticals to carry the agents to and concentrate the agents in the tumors and (3) neutron energy spectra, irradiation flux and irradiation time appropriate for effective cancer therapy. In particular, boron-10 has been found to be well suited as a targeting agent for neutron capture therapy. In this reaction, owing to its non-toxicity and high capture cross section, a low energy neutron captured by boron-10 yields two charged particles, an alpha particle and a lithium ion, with sufficient energy to kill cells, yet the charged particles travel only about 10 microns-about the diameter of an average cell. As a result, the lethality of the neutron capture is limited to the cells adjacent the location of boron atoms and does not affect healthy tissues nearby.

Particularly since the early 1960's, there has been significant progress in the development of boron containing targeting agents. One compound, polyhedral borane ($NA_2B_{12}H_{11}SH$, abbreviated as "BSH") has been used with some success in human trials conducted by Dr. Hiroshi Hatanaka at Teikyo University in Tokyo. Using this compound, Hatanaka has reported tumor to blood concentration ratios of boron-10 of up to 2, and with an average boron-10 concentration of 26.3 microgram/gram in the tumor and has treated about 100 patients. Using a reactor source of thermal neutrons, Hatanaka has achieved a three-fold increase in patient survival time. See:

Hatanaka, H., "Boron Uptake by Human Brian Tumors and Quality Control of Boron Compounds," in "Boron-Neutron Capture Therapy of Tumors," edited by H. Hatanaka, Nishimura Co., Ltd., p. 77 (1986)

Hatanaka, H., "Clinical Experience of Boron-Neutron Capture Therapy for Gliomas-A Comparison with Conventional Chemo-Immuno-Radiotherapy," in Boron Neutron Capture Therapy for Tumors, edited by H. Hatanaka, Nishimura Co., Ltd., p. 349 (1986). Several new boron-10-containing compounds have been developed and some of them have been tested with animals. Promising compounds which have been tested in tumor-bearing animals include $NA_4B_{24}H_{22}S_2$ (or BSSB, the dimer of BSH), and a boronated amino acid called p-boronphenylalanine (or BPA). Other new antibodies, nucleosides, low-density lipoprotein, and liposomes have been investigated. Among them, porphyrins have already shown therapeutic efficacy in treating tumor-bearing animals with NCT. While BSH has shown therapeutic efficacy in human glioma, BPA and prophyrin are the two prime candidates which may eventually make NCT a widely used modality in treating human malignant tumors other than glioma. See the following publications in connection with the above.

Joel, D. D., et al., "Pharmacokinetics and Tissue Distribution of the Sulfhydryl Boranes (Monomer and Dimer) in Glioma-Bearing Rats," Strahlenther, Onkol., Vol. 165, p 167 (1989)

Coderre, J. A., et al., "Selective Delivery of Boron by the Melanin Precursor Analogue p-Boronphenylalanine to Tumors Other than Melanoma," Cancer Research 50, p 138 (January 1990)

In addition to the progress made in the development of boron-10 targeting agents, significant advances have been made in the field of accelerators as an alternative to the use of reactors. Accelerator technology currently allows the generation of a proton beam of the requisite energy level and intensity (i.e., beam current). It also is known that if a lithium target is bombarded with a proton beam of the requisite energy level and intensity, a neutron beam can be produced. However, in order to be useful for boron neutron capture therapy, this neutron beam must be moderated in order to lower the energy level of the neutrons from the 100 keV to 800 keV range to the 1 eV to 10 keV range. Moderator systems for reducing the neutron beam energy levels to the desired range have been designed and experimentally proven, and utilize materials such as beryllium oxide, aluminum oxide and heavy water (i.e., $D_2O$).

However, cooling systems heretofore employed for the removal of very high heating loads and high heat fluxes have been limited. One approach uses the latent heat of vaporization of lithium in order to remove the heat generated by the bombarding proton beam by boiling the lithium target. This scheme for target cooling has two limitations. First, the chamber containing vaporized lithium must be continuous with the evacuated channel leading to the proton accelerator. As a result, unwanted lithium vapor leakage into the accelerator chamber is unavoidable. Second, in order to transfer the requisite amount of heat, the lithium target must be operated at temperatures above 900° C., a requirement which presents significant operational and safety problems for use in hospital-based therapy sites.

Another approach to the generation of neutrons for neutron capture therapy is described in U.S. Pat. No. 4,666,651. The approach utilizes a neutron generator to generate charged particles having an energy of at least 15 MeV. These particles are directed at a lithium deuteride target which is cooled by the circulation of gas which is chemically non-reactive with the lithium deuteride target. However, as the high heat fluxes associated with the generation of high intensity neutron beams preferred for neutron capture therapy (viz. 500 to 1500 watts/cm$^2$), the use of gas cooling is limited due to high target temperatures, high exit gas temperatures and large gas flow rates.

Previous target cooling systems have included the use of liquid-cooled stationary targets as illustrated in U.S. Pat. No. 4,599,515 by Whittemore, and U.S. Pat. No. 4,192,998 by Azam. However, the high heat fluxes (500 to 1500 watts/cm$^2$) associated with the above high intensity neutron irradiation systems exceed the heat dissipation capability of existing stationary, liquid-cooled targets. As a consequence, preferred target materials such as lithium cannot be effectively used as the target temperature where high heat fluxes greatly exceed the melting point resulting in unwanted evaporation of the target (e.g., lithium). Others have attempted to increase the effectiveness of target cooling by rotating the target material (e.g., beryllium or lithium) relative to a stationary beam of protons or deuterons. (See U.S. Pat. No. 4,582,667 by Bauer; U.S. Pat. No. 4,360,495 by Bauer; U.S. Pat. No. 4,112,306 by Nunan; and U.S. Pat. No. 4,090,086 by Cranberg.) However, all such targets have been designed for the production of high energy neutrons using an incident beam of high energy ions (e.g., protons or deuterons), such neutrons having energies in the range from several hundred keV to several GeV and higher. As a consequence of the objective of producing high energy neutrons, target cooling systems have not excluded hydrogenous coolant fluids (e.g., water) from the forward beam of neutrons since small layers of hydrogenous materials will not result in a significant attenuation of the neutron beam produced. In the case of Bauer (U.S. Pat. Nos. 4,582,667 and 4,360,495), the target material forms a matrix through which a liquid coolant flows.

Also, earlier target and target cooling designs provide no technique for containment of low melting temperature target materials such as lithium. In addition, those methods do not consider the importance of maintaining rotational speed of rotating targets on the containment of target materials when heated to temperatures above their melting point.

SUMMARY

The present invention is addressed to an apparatus and system for generating neutrons wherein a generating source of charged particles is employed to react with a neutron generating target in a uniquely cooled and sub-atmospherically contained component assemblage. Target material, such as lithium metal, is mounted upon a rotating carriage which, for one embodiment, movably positions it within the pathway of the charged particle or ion stream without the intervention of windows or the like. Cooling of the target region is carried out through utilization of the centrifugal forces which are generated by a rotation of the target carriage to urge fluid coolant into a proper position adjacent the target while posing no effective interference to generated neutron flow. In an embodiment, the target material such as lithium metal, is retained within a capsule mounted upon the rotating cardage and has an upwardly disposed foil or equivalent surface of thickness and low atomic number material such as aluminum posing no substantial interference with ion interaction with the encapsulated target material. Preferably, the capsules are formed with the target material in a vacuum environment. As a consequence of the highly efficient cooling approach of the invention, the very large heating loads and target heat fluxes of approximately 1,000 watts/cm$^2$ can be accommodated while maintaining the lithium at very low vapor pressures corresponding to target temperatures at or below the melting point of the target material, (e.g. lithium).

The neutrons produced by collisions of the ions (e.g. protons) with the target material are moderated by the selective use of geometries and materials associated therewith to achieve a neutron beam having energies in a range suitable for use in neutron capture therapy.

Another feature of the invention is to provide apparatus for generating neutrons which comprises a particle source having an output of charged particles directed along a predetermined pathway. A containment chamber is provided for receiving the output of charged particles under sub-atmospheric pressure and a target carriage is mounted for rotation about a carriage axis within the containment chamber. The target carriage has a target support region movable across the pathway and has an internally disposed, confined cooling chamber extending into adjacency with the target support region. A circulation conduit assembly is provided having one end in fluid sealed connection with the target carriage assembly coolant chamber and extends outwardly from the containment chamber to a port assembly. A target assembly retaining neutron deriving target material is located at the target support region and is reacted with the charged particles within the pathway to generate neutrons and heat, and a fluid coolant for circulation to the coolant chamber through the circulation conduit assembly is provided.

Another feature of the invention is to provide apparatus for generating neutrons which comprises a particle source having an output of particles directed along a predetermined pathway. A target cardage is provided which is mounted for rotation about a cardage axis and which has an outer periphery and a target support region extending inwardly from the periphery. A target assembly is provided which includes a plurality of capsules mountable upon the target carriage at the target support region, each capsule being formed having a cavity within which a meltable neutron deriving target material is disposed. Further, each cavity is sealingly covered by a thin material overlay having a thickness and atomic number selected to permit substantial passage of the charged particles therethrough for impingement upon the target material to effect neutron generation. A cooling arrangement is provided for removing heat generated at the target support region by the charged particle impingement.

Other objects of the invention will, in part, be obvious and will, in part, appear hereinafter The invention, accordingly, comprises the system and apparatus possessing the construction, combination of elements, and arrangement of parts which are exemplified in the following detailed disclosure.

For a fuller understanding of the nature and objects of the invention, reference should be had to the following detailed description taken in connection with the accompanying drawings.

DETAILED DESCRIPTION OF THE INVENTION

In the discourse to follow, initial embodiments of the accelerator based neutron irradiation system of the invention are described which look to the location of neutron deriving target material such as lithium or beryllium upon a rotating target. The target material, when reaching a liquid phase due to the thermal activity associated with ion bombardment, is retained through employment of a surface tension based configuration of the retention structure associated with the target. In a later, preferred embodiment, a highly practical approach to retaining the target material is described. In the latter regard, the lithium or other target materials must be retained for the instant system within a vacuum environment. Additionally, during manufacture or maintenance of the system, the lithium target material will react at room temperature with air, for example, and thus must be protected during periods of system inactivity. For all embodiments, the target region is cooled through utilization of highly effective techniques and the neutrons generated are moderated to energy levels considered ideal, for example, for the therapeutic applications contemplated.

Figure 1:
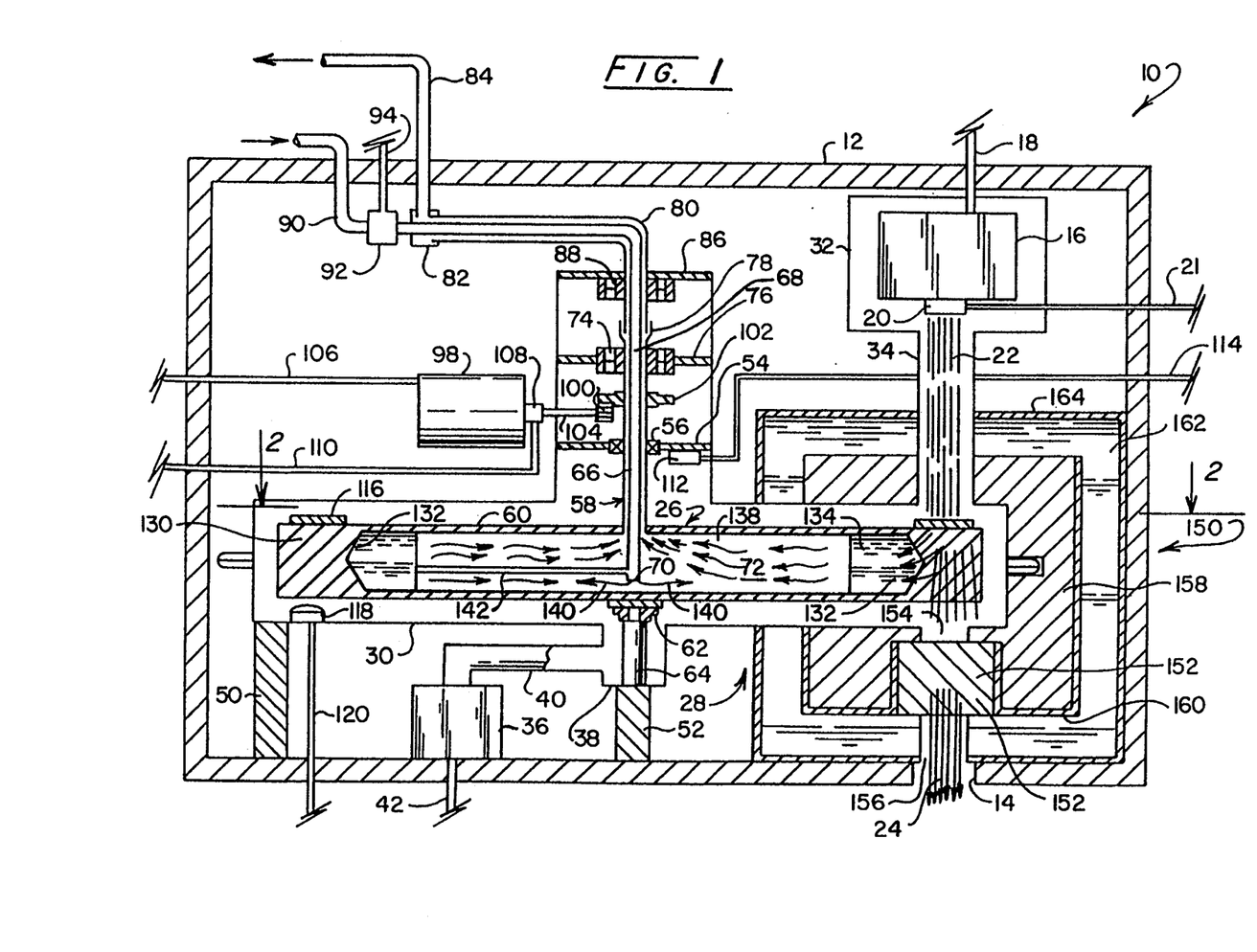
FIG. 1 is a schematic, partially sectional view of apparatus for generating neutrons according to the invention.

Referring to FIG. 1, an initial embodiment of the apparatus of the invention is represented generally at 10. The apparatus 10 is seen to be retained within a housing 12 having an opening 14 formed therein through which neutrons at and above the epithermal neutron range may project for use, for example, for the noted therapeutic purposes. Housing 12 may be formed, for example, of metallic and/or masonry materials such as concrete or cinder block. As such, the housing serves to isolate the system components from operating personnel as well as a patient during conventional use. Within the housing 12, there is disposed a particle source 16 coupled as represented at cabling as at 18 with the power source. This source 16 also may be positioned upon or outside of the housing 12. The output of the source 16 is monitored by a current monitor 20 having a monitor output at line 21. The generated charged particles or ions occur as a stream at 22 extending along a downwardly directed pathway.

A preferred form of particle source 16 is an accelerator utilizing radio-frequency quadruple (RFQ) acceleration technology. Such systems are produced, for example, by AccSys Technologies, Inc., Pleasanton, California. Of course, Van de Graaff accelerators also are available. In general, the device 16 must produce a beam of ions such as protons of adequate energy to develop the requisite neutron energies upon impingement with the target material of the system. In the case of a lithium target, the system seeks the nuclear reaction:

*lithium 7+proton→beryllium 7+neutron*

In order to reach a sufficiently high yield of neutrons, the incident proton energy at a target impinged upon by beam 22 should be on the order of 2.5 MeV. Higher energy levels also will provide high neutron yields, but subsequent interactions of higher energy neutrons produced with other materials in the system will produce high levels of unwanted gamma radiation. Hence, to permit efficient generation of neutrons with the use of a proton beam on a lithium target, while minimizing unwanted secondary gamma radiation, the noted energy levels should be approached. The resultant neutron beam depicted by the arrows 24 emanating from opening 14 must have an energy spectrum suitable for boron neutron capture therapy and an intensity sufficiently high to permit irradiation treatment sessions of practical duration. Based on the (1) characteristics of candidate boron-containing neutron capture agents, (2) the moderator system employed, (3) 2.5 MeV proton beam energy, the incident proton beam intensity needs to be, for example, in the range from about 15 milliamps to 50 milliamps.

For the case where beryllium target material is employed, the system seeks the nuclear reaction:

*beryllium 9+proton→boron 9+neutron*

In the case of beryllium 9, in order to reach a sufficiently high yield of neutrons, the incident proton energy should be on the order of 4.0 MeV. Based on the same considerations as discussed above for lithium target materials, the incident proton beam intensity needs to be in the range of about 15 milliamps to 50 milliamps.

Looking to the requirements for the output of the system at neutron beam 24, for the case of boron neutron capture therapy, the neutron energy spectrum should be in the range of from 1 eV to 10 keV and preferably, in the range of from 10 eV to 1 keV. In order to minimize unwanted radiation damage, secondary radiation sources such as gamma radiation, as noted above, should be maintained as small as possible with associated gamma energies maintained as low as possible. In order to allow radiation treatment periods of manageable length, the flux of neutrons having the appropriate energy spectrum as discussed above should be approximately $3 \times 10^8$ to $1.5 \times 10^9$ neutrons/cm$^2$/second.

The accelerator 16 as well as its ion output beam 22 and the assemblage of target components including a target carriage 26 are enclosed within a containment chamber represented generally at 28. Chamber 28, within which a vacuum is maintained, includes an annular or cylindrical chamber portion 30 within which the target carriage 26 is mounted, an accelerator retaining portion 32 within which the accelerator 16 is mounted; and a pathway encompassing portion 34 surmounting the ion beam 22 and extending directly to annular chamber portion 30 over the target material mounted upon carriage 26. Located beneath the annular chamber portion 30 of the containment chamber 28 is a vacuum pump 36 shown coupled to a lower extension 38 of portion 30 via conduit 40. Controlling power input to the pump 36 is represented at cabling 42.

In general, the accelerator or charged particle source 16 will call for a vacuum pumping system which includes a diffusion pump and cold trap to assure a vacuum level of approximately $1 \times 10^{-6}$ torr at the entrance of the pathway encompassing portion 34 of containment chamber 38. The vacuum level within the pathway encompassing portion 34 at the surface of the target within annular chamber portion 30 can be lower, i.e. pressure can be higher. For example, a vacuum level of $1 \times 10^{-3}$ torr to $1 \times 10^{-4}$ torr at the target region is adequate. The vacuum level within the annular portion 30 encompassing the target carriage assembly 26 can be generated utilizing mechanical pumping. For example, a Welch Model No. 1397 pump as described in Fischer Scientific Catalog No. 01-100-15 may be employed.

Containment chamber 28 is maintained in position by supports as at 50 and 52, and the upwardly disposed central region thereof is closed by a seal structure including a rotating vacuum seal 56 which serves to rotatably support an upstanding cylindrical conduit and rotating drive component 58. The vacuum seal 56 may be provided, for example, as a type CR24892 bearing seal produced by CR Industries, Elgin, Illinois. This device performs in conjunction with a ball bearing flange block, type MF4E-247 marketed by Browning Company.

The cylindrical drive component 58 extends to and is coupled with the upper surface 60 of target cartage 26. As such, the drive 58 can impart a rotational motion to the structure 28 as it resides within the vacuum environment of the annular chamber portion 30. To support the disk-shaped structure 26 at the opposite side of its axis extending through the middle of component 58, a thermally isolated thrust bearing 62 is coupled thereto coaxially with component 58 which, in turn, is mounted upon a support 64 within lower extension 38 of the containment chamber portion 30. A variety of thrust beatings are available for the function at beating 62, for example, a bearing identified as FAG #53213 along with a seating ring identified as a type FAG #U213 produced by FAG Bearings Corporation of Stamford, Connecticut. Thus rotatably supported, the disk shaped target cartage 26 may rotate within a vacuum environment for the purpose of positioning target material before the charged particle or ion stream 22.

Looking to the technique by which rotation is imparted to the carriage 26, it may be observed that drive component 58 is formed of two parts, an outer, rotating drive cylinder 66 which is rotatably engaged by the bearing seal 56, and an inner, stationary cylindrical conduit part 68 which is seen extend downwardly to an opening 70 within an interior, sealed chamber 72 of the target cartage 26. Outer drive cylinder 66 is further supported by a bearing 74, the outer race of which, in turn, is supported by support component 76. Drive cylinder 66 then terminates at a swivel pipe joint 78. Swivel pipe joint 78 may be provided, as a type OPW style 20-F marketed by the OPW Division of Dover Corporation, Mason, Ohio. With the arrangement shown, the drive cylinder component 66 may rotate while remaining in sealed fluid communication with a stationary conduit 80 which will be seen to function to exhaust steam or the like outwardly via a coupling 82 and conduit 84. Conduit 80 is supported by a top flange 86 and support block 88, and is seen to have substantially the same inner and outer diameter configuration as drive cylinder 66. In the latter regard, the inner diameter of these components is selected so as to provide sufficient inner diameter to outer diameter spacing with respect to conduit 68 to permit the flow of a cooling fluid between (e.g. flow of steam generated within chamber 72). Note that a cooling input is represented at conduit 90 extending through an electrically controlled valve 92 with appropriate control inputs 94. Valve 92 is coupled to the opposite end 96 of stationary conduit 68 and may be provided, for example, as a Model SV287 flow valve marketed by Omega Engineering, Inc.

Rotational drive is imparted to the drive cylinder 66 from an electric motor assemblage 98 performing in conjunction with paired miter gears 100 and 102, the latter being fixed to drive cylinder 66, and the former being drivably coupled to the shaft 104 of motor assemblage 98. Gears as at 100 and 102 may be provided, for example, by Emerson Electric Company, Browning Manufacturing Division, Maysville, Kentucky. Motor assemblage 98 may be provided by the same organization as a motor-reducer combination which is described in catalog no. 450C1-40FEX 7/8 with 200A 3P23, 2 horsepower motor exhibiting 2074 in.-lb. torque. Power input to the assemblage 98 is represented at cabling 106 which may provide such power in combination with a motor starter, for example, a type 109-A18AA3 marketed by Allen-Bradley, a Rockwell International company of Milwaukee, Wisconsin. Additionally coupled to the shaft 104 is a tachometer 108 for monitoring rotational speed. Device 108, seen coupled with an input-output control line 110, may be provided as a slow speed digital tachometer system, Model No. SSA-50P-1 having a 4 to 20 milliamp current loop for external monitoring of rotational speed and associated control functions. Such a device is marketed, for example, by Electro-Sensors, Inc. of Eden Prairie, Minnesota.

The vacuum level within the containment chamber 28 is monitored by a vacuum level sensor 112, the output of which is represented at cabling 114. Sensor 112 may be provided, for example, as a VWR Scientific Model No. EVD021-66-000 which may perform with a microprocessor driven control unit marketed under Catalog No. EVD386-13-000 by the same organization.

Temperatures at the annular target region 116 of the target carriage 26 are generally monitored by a temperature sensor 118 which is disposed beneath the region 116 at a location remote from the region of impingement of ion beam 22. Located within the annular chamber portion 30 of the containment chamber, the device 118 develops a temperature related output signal at line 120 and may be provided, for example, as an infrared, non-contact temperature monitoring device Model No. OS 1200-LTS-B-N4 marketed by Omega Engineering, Inc., Stamford, Connecticut. In the event of excessive temperatures at the target region 116 as detected from device 118, a control system employed with the apparatus provides a signal warning to the operator and interrupts operation of the accelerator 16. The same form of warning and accelerator 16 interruption may be provided in conjunction with a detection of inadequate vacuum at gauge 112.

The amount of thermal energy generated in conjunction with such beam impingement systems may be relatively high, for example at the 75 kilowatt level. Thus, a technique is required for accommodating such thermal phenomena to an extent protecting the target. Looking additionally to FIG. 2, it may be observed that the annular target region 116 is rotated within vacuum before the beam 22 pathway. As this occurs, resultantly developed neutrons pass through an aluminum outer substrate 130 located immediately beneath the target region 116, aluminum having a sufficiently low neutron capture attribute. Heat generated by the system is witnessed at an internally disposed heat exchange surface region 132 as represented by arrows extending therefrom. Against the surface or region 132 there is maintained a coolant fluid 134 which, for the instant embodiment, may, for example, be water. Coolant 134 is maintained in position as shown by the centrifugal force evoked in consequence of the rotation of target carriage 26 by motor assemblage 98. Under the influence of heat, the coolant 134 changes from a liquid phase to a vapor phase, the latter of which exits through a circulation coolant assembly conduit 84 as represented at arrows 138. Make-up coolant such as water may then be introduced into the chamber 72 through conduit 90 under the control of valve 92. Water exiting for this purpose is represented at arrows 140. To provide a continuous monitoring of the level of water at 134, particularly with respect to its radial extent from the axis of drive component 58 and the target carriage 26, a stationary water level detector 142 is fixed to the stationary conduit 70 and is of length sufficient to engage at least the outer surface of liquid phase coolant 134 at its lowest acceptable quantity. A variety of liquid level sensors are available for this purpose, one, for example, being a probe Model No. EHT-183-A2 and an associated liquid level controller marketed as Model FLT-2011 by Lumenite Electronic Company of Franklin Park, Illinois. Cabling from the sensor 142 preferably is directed through the stationary conduit 68 whereupon it may be led from the system via the junction at valve 92, for example with cable 94.

A moderator and containment assembly surmounting ion beam 22 and the target carriage 26 at the location of the ion beam 22 is represented generally at 150. Assembly 150, as seen additionally in FIG. 2, includes a moderator 152 which serves the function of altering the neutron energies generated at target 112 to a level most suited for the therapeutic purposes at hand. The material at moderator 152 preferably is selected having a large neutron scattering cross-section, a small neutron cross section for radioactive neutron capture, and the capability to decrease the amount of neutron energy with each neutron collision. In general, neutron energy is reduced as it progresses through the moderator 152 with the incoming neutron energies at neutron inlet 154 being in a range of 100 keV to 800 keV at the exit side of target region 112 and, in general, at the neutron inlet 154. Following moderation at moderator 152, neutron energies at the outlet channel 156 preferably are in a range of 1 eV to 1 keV.

Generally, neutrons are designated according to their energies, including the following:

Thermal neutrons in thermal equilibrium with the substance in which they exist: Most commonly neutrons of kinetic energy of about 0.025 eV, which is about $\frac{2}{3}$ of the mean kinetic energy of a molecule at 15° C. Generally thermal neutrons are undesirable for the instant therapeutic application inasmuch as they react with tissue;

Epithermal neutrons, or neutrons having energies just above those of thermal neutrons: The epithermal neutrons' energy range is between a few eV and about 1000 eV;

Fast neutrons which are neutrons with energies exceeding 100,000 eV, although sometimes a lower limit is given. In connection with the above, see generally Van Nostrand's Scientific Encyclopedia, 5th Edition, p 1611.

Exemplary materials for use as a moderator 152 are beryllium oxide (BeO), deuterium oxide ($D_2O$) and mixtures of aluminum and deuterium oxide.

Figure 2:
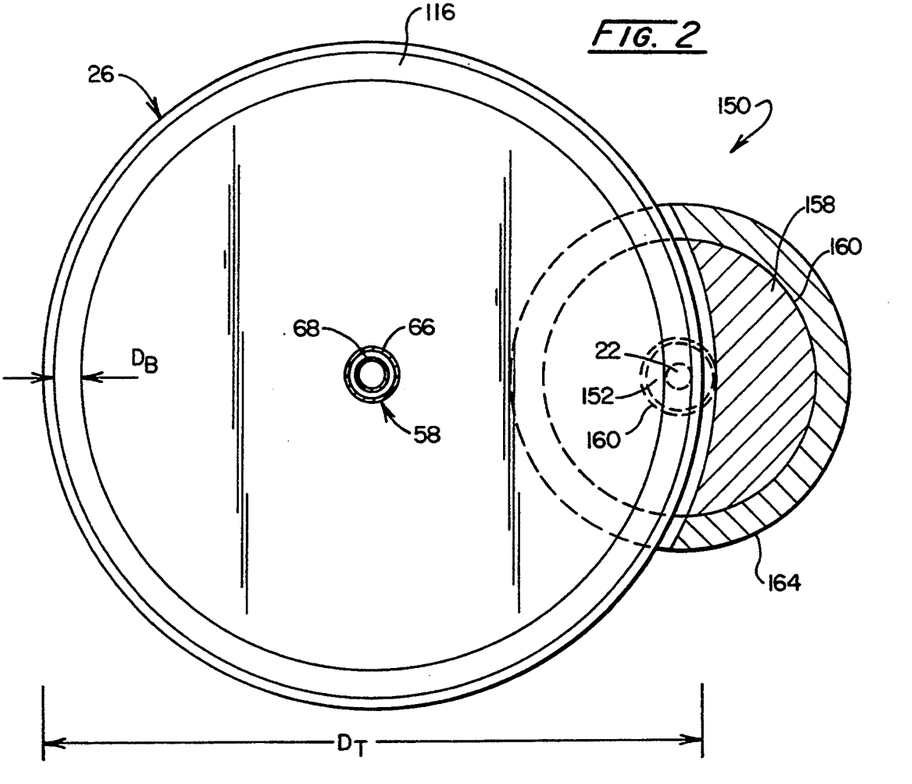
FIG. 2 is a cross-sectional view taken through the plane 2—2 shown in FIG. 1.

Located adjacent to and surrounding the moderator 152 as well as those regions of the annular chamber portion 30 of the containment chamber in the vicinity of the beam 22, target 112, and moderator 152, is a reflector 158. Reflector 158 preferably will be formed of materials having a large neutron scattering cross section and will function to reflect such neutrons with a small amount of energy decrease. Thus, epithermal neutrons are reflected a short distance without significantly reducing their energy. Generally, the reflection will be of neutrons having energies greater than epithermal electrons. This increases the efficiency of the neutron generating system. A material meeting the criteria for reflector 158 is alumina ($Al_2O_3$). Due to alumina's large cross section for radioactive capture of thermal neutrons, it is preferable to place a layer of lithium-6 (6Li) at the boundary between the moderator 152 and reflector 158. This layer is represented at 160. Next outwardly from the reflector 158 and layer 160 is a neutron absorber 162 which functions to capture neutrons which may be emitted from the reflector 158 except at the outlet channel 156. The absorber 162 also should minimize the generation of gamma radiation. Absorber 162 may, for example, be provided as deuterium oxide ($D_2O$) which preferably will be filled with 2,000 ppm boron 10 which, in turn, has a very high neutron cross section. That quantity of boron 10 will be soluble in the heavy water at the absorber 162. Next outwardly from the neutron absorber 162 is another layer 164 of lithium-6 (6Li). This layer or coating captures any neutrons emitted from the heavy water. Collectively, the moderator and containment assembly 150 permits the emission of neutrons of desired energy range through the outlet channel 156 while minimizing the exit of neutrons or gamma rays from all other regions of the accelerator neutron irradiation system.

The preferred target material for the target region 116 of the instant invention is lithium metal. Under the ionic bombardment contemplated, this lithium metal may enter a liquid phase in view of its relatively low melting point in the order of 180° C. Thus, while the target carriage 26 is rotated to maintain fluid coolant 134 against the heat exchange surface 132, accommodation must be made to retain lithium metal, which must be considered melted or in a fluid phase at its proper target location for neutron generation. Additionally, it is necessary that a sufficient area or associated quantity of lithium be introduced to the ion beam pathway 22 both to control temperature and to generate adequate neutron flux. Generally, the carriage 26 will rotate between 30 rpm and 60 rpm, and the area generally presented at region 116 may be represented as follows:

$$A = \pi/4[D_T^2 - (D_T - D_B)^2],$$

where: A equals the area of target region 116;
$D_T$ is the outer diameter of the region 116; and
$D_B$ is the radial extent of the target region 116 or, alternately, the corresponding radial extent or diameter of the ion beam pathway 22.

Figure 3:
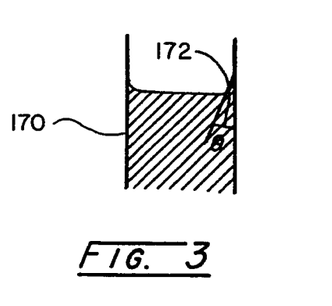
FIG. 3 is a schematic representation of an attractive form of liquid surface tension.
Figure 4:
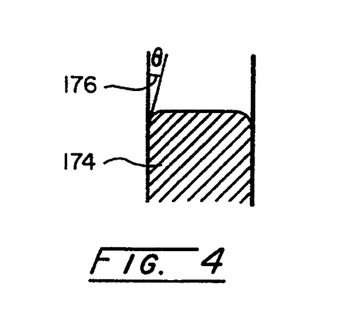
FIG. 4 is a diagrammatic representation of a repulsive form of liquid surface tension.

To retain the target material such as lithium in position for neutron generation while accommodating necessary centrifugal forces required to achieve cooling within the target carriage 26, the initial embodiment of the invention looks to a target retention structuring which is dimensioned and configured to achieve a surface tension value for the lithium target material when in a liquid phase which effectively matches or overcomes the centrifugal forces resulting from target carriage 26 rotation. In general, when a liquid is in contact with a solid surface, molecules in the liquid adjacent to the solid will experience forces from the molecules of the solid in addition to the forces from other molecules in the liquid. Depending upon whether these solid/liquid forces are attractive or repulsive, the liquid solid surface will curve upwards or downwards. Looking momentarily to FIG. 3, a liquid-solid interface is depicted, the exemplary liquid being represented at 170. For this example of FIG. 4, the forces are attractive and the liquid. 170 is said to "wet" the solid. The angle made by the liquid 170 surface with respect to the container is known as the angle of contact, Θ. This angle of contact Θ in the example of FIG. 4 is shown at 172. The corresponding angle of contact for repulsive forces are represented at liquid 174 in FIG. 4 and contact angle Θ at 176.

Figure 5:
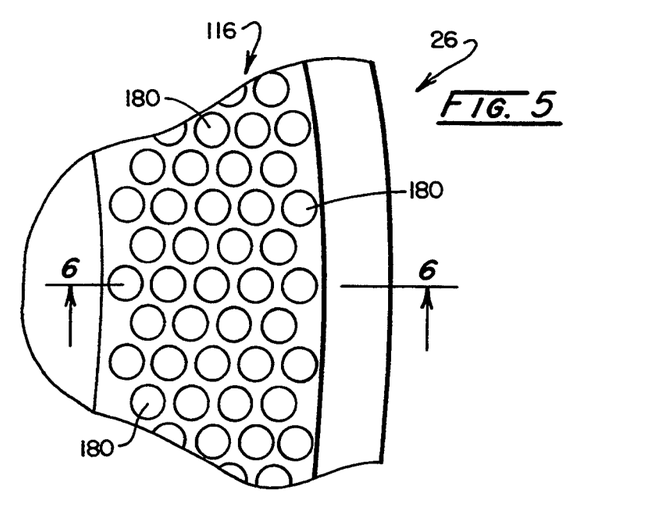
FIG. 5 is a partial sectional view of a target region structural embodiment according to the invention.

Referring to FIG. 5, a geometry for retaining lithium metal at the target region 116 is revealed. In this embodiment, the target region 116 is fashioned having a plurality of downwardly extending intersticed cavities, certain of which are revealed at 180. By selecting the effective diameter of these cavities 180, which for the present embodiment will be the actual geometric diameter thereof, the value of surface tension may be designed to meet the rotational forces being encountered. To provide for an attractive interrelationship between lithium metal and the retaining structure, the interior surfaces of the cavities 180, which achieve a sufficiently small contact angle, 0, for achieving good wetting, or the material from which they are formed, should be chemically compatible with lithium metal. Metals and alloys which meet these requirements include, for example, molybdenum based alloys containing 0.5% titanium and 0.1% zirconium (TZM alloy); niobium-based alloys containing zirconium; tantalum alloys containing tungsten (e.g. tantalum with 10% tungsten); and tungsten.

Figure 6:
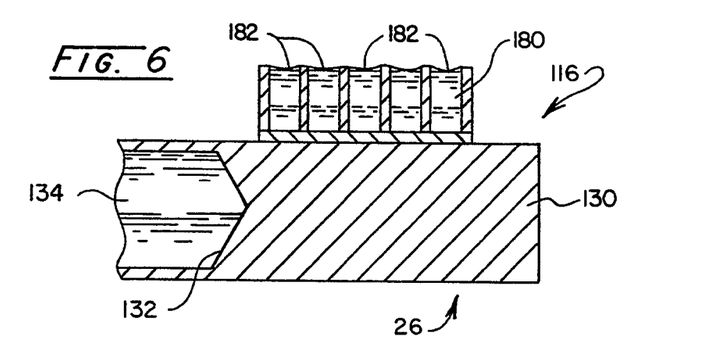
FIG. 6 is a sectional view taken through the plane 6—6 in FIG. 5.

Referring to FIG. 6, the structure represented in FIG. 5 is revealed in sectional fashion. Note that the cylindrical cavities 180 are seen to be filled with a liquid lithium metal represented at 182.

Figure 7:
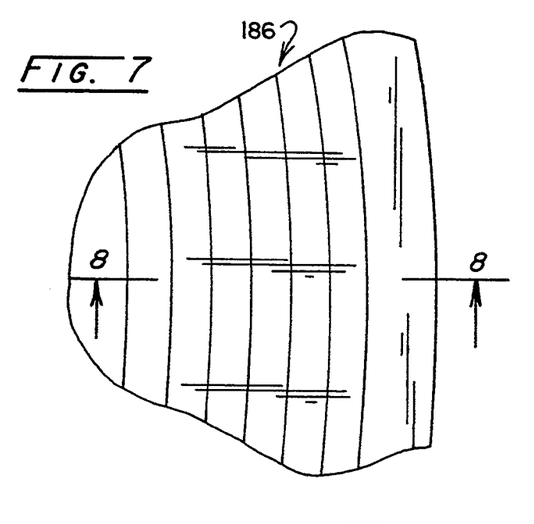
FIG. 7 is a top partial view of another target structural embodiment of the invention.
Figure 8:
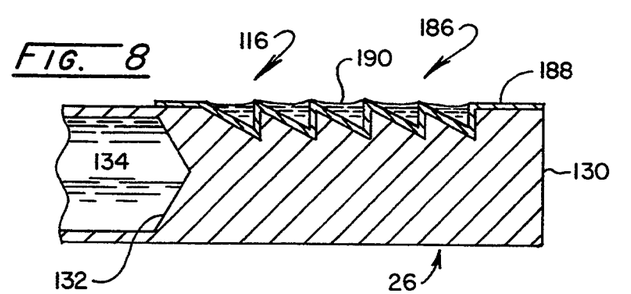
FIG. 8 is a sectional view taken through the plane 8—8 in FIG. 7.
Figure 9:
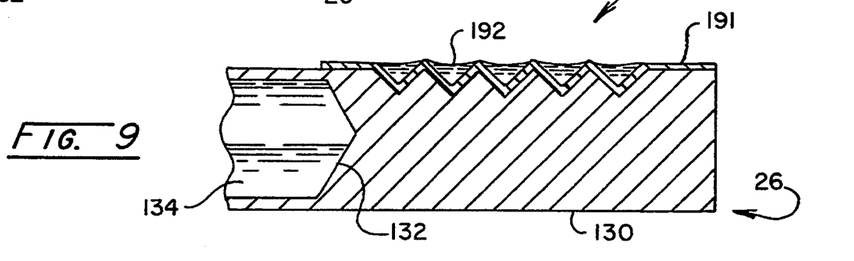
FIG. 9 is a sectional view of another embodiment for a target region according to the invention.

Referring to FIGS. 7 and 8, the intersticed cavities of the target region 116 may be formed as inwardly extending concentric grooves as represented in FIG. 7 in general at 186. The concentric grooves 186 may be formed, for example, having a radially disposed cross section corresponding with an inverted scalene triangle. This configuration is represented in FIG. 8. Looking to that figure, a coating or layer of the preferred target retaining metal material is represented at 188 and the lithium metal is shown within the concentric grooves at 190. Other configurations will occur to a designer, for example, looking additionally to FIG. 9, the grooves are shown in conjunction with coating or layer 191 being formed to have a radially disposed cross section corresponding with an inverted isosceles triangle. The liquid lithium metal is represented in the drawing at 192.

The computation of requisite surface tension as well established may be expressed as follows:

$$P_c = (2\sigma \cos\Theta)/D_c,$$

where:
Θ is the contact angle;
$P_c$ is resultant surface tension "capillary" pressure; and
$D_c$ is the characteristic dimension or effective diameter of the interstices being evaluated.

Of course, other geometric configurations such as hexagons and the like may be employed with the liquid target metal retention approach. The design is predicated upon the development of a retention force which is equal with or exceeds the centrifugal force occasioned with the revolution of target carriage 26. For a further discussion of surface tension, reference is made to the publication "Heat Pipes", Second Edition by P. Dunn and D. A. Reay, Pergamon Press, New York, pp 22–28 and 302.

In general, with the instant system, the rotational speed of target carriage 26 is selected to be sufficiently large to maintain the working fluid or coolant in contact with the heat exchange surface or region within the radial extremities of the cavity 72. However, the speed also must effectively distribute the heat generated at the target regions 116. However, the rotational speed also should be selected to be no higher than necessary to meet those two requirements, inasmuch as the higher the rotational speed, the greater the centrifugal force acting on the liquid lithium target and consequently, the smaller the allowed characteristic dimension or diameter $D_c$ of the interstices retaining the liquid.

Figure 10:
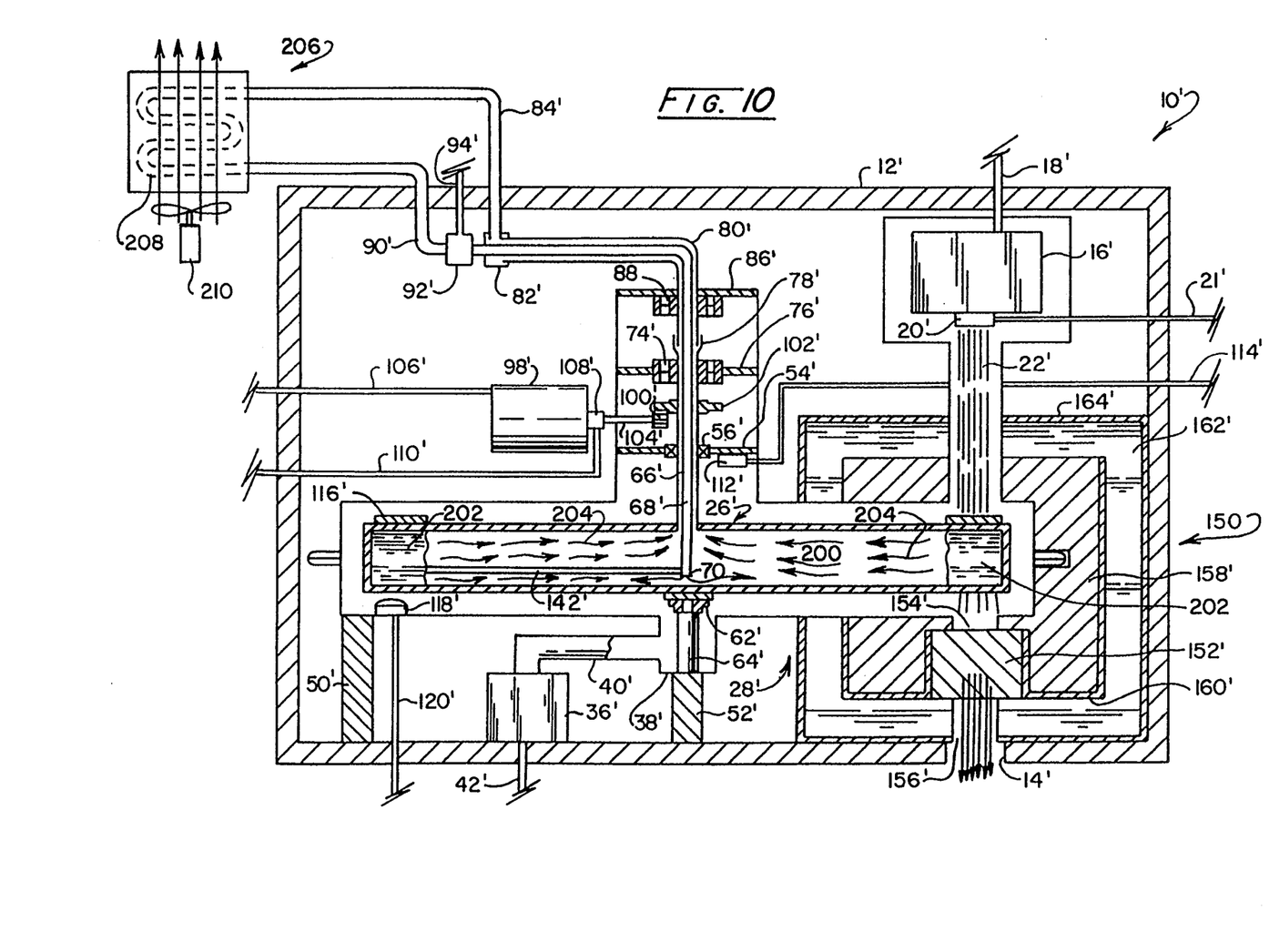
FIG. 10 is a schematic partially sectional view of the apparatus of the invention showing an additional cooling system embodiment.

Referring to FIG. 10, another embodiment for the technique of cooling target 26 is revealed. The components of FIG. 10 will be seen to be quite similar and, for the most part, identical to those shown in FIG. 1 with the exception of the noted cooling components. Accordingly, parts having commonality between the figures are shown in FIG. 10 with identical numeration but in primed fashion. Looking to FIG. 10, the fluid selected for cooling is heavy water or deuterium oxide (D$_2$O). Because of the low capture cross section of that fluid, it may be permitted to accumulate in the fluid phase at a radial distance from the axis of carriage 26′ such that it is located substantially beneath the pathway of ion beam 22′. Note, in this regard, that the cavity of carriage 26′, now identified at 200, extends essentially to a heat exchange region located substantially beneath the target support region 116′. This fluid accumulation is represented at 202. The accumulated heavy water at 202 resides in heat transfer relationship with the interior surface of cavity 200, especially as that surface is present beneath target region 116'. Generally at that surface within the cavity, a transition to vapor phase occurs, and as represented by arrows 204, this vapor phase is conducted through conduits 80' and 84' to a condenser 206. The coils shown in phantom within condenser 206 at 208 are cooled as represented by the fan symbol 210 and liquid phase fluid returns to the system via conduit 90' under the control valve 92'.

Figure 11:
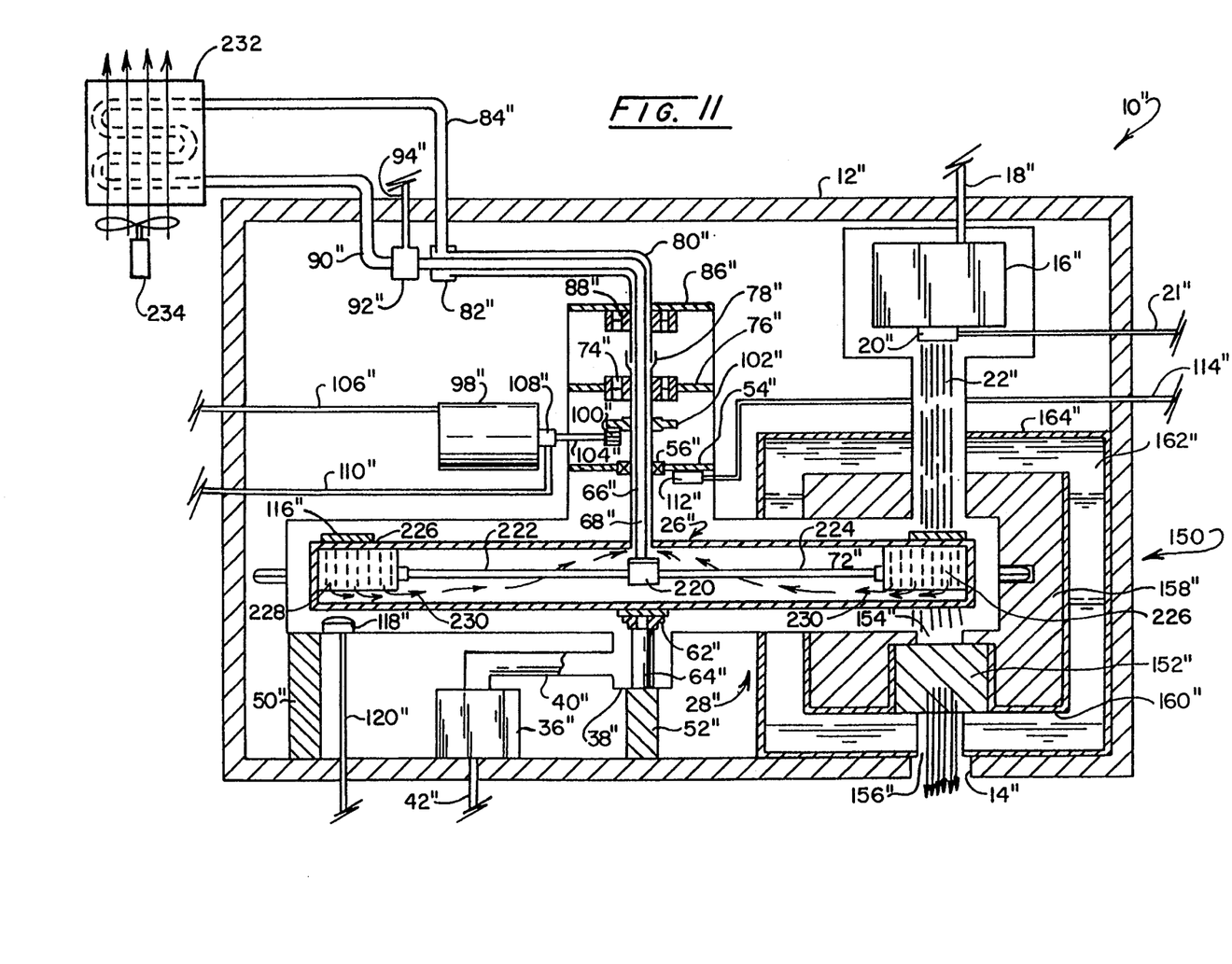
FIG. 11 is a schematic, partially sectional illustration of another embodiment of the apparatus of the invention.
Figure 12:
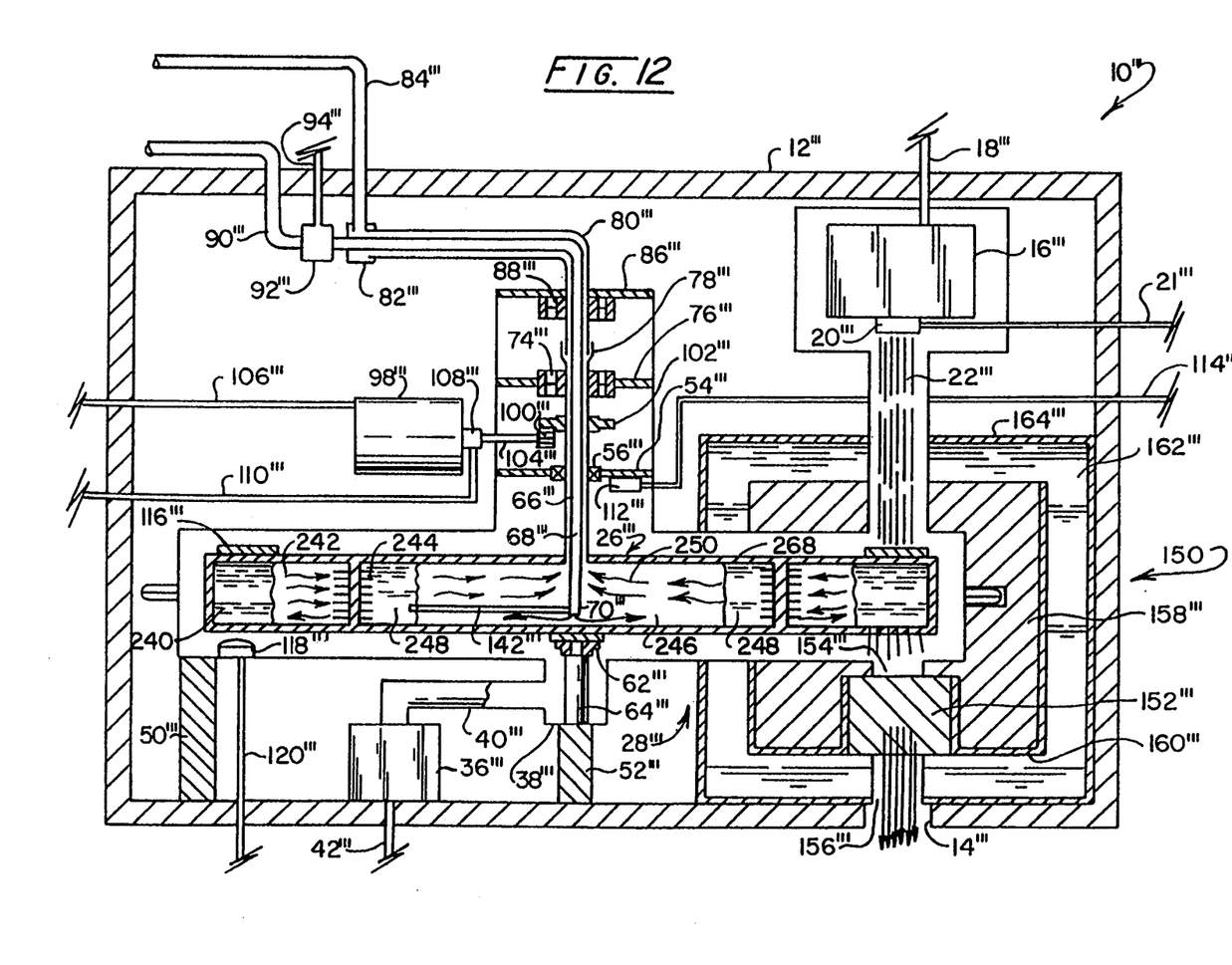
FIG. 12 is a schematic, partially sectional illustration of the apparatus of the invention showing still another embodiment for the cooling system thereof.

Fluid cooling also can be carried out with the target carriage 26 utilizing a coolant which remains in a gaseous phase. Such a coolant may, for example, be selected as helium, a substance which may be introduced directly beneath the target region 116 without adversely affecting the flow of neutrons toward the outlet channel 156 as in the case of aluminum material. Referring to FIG. 11, an implementation of the apparatus 12 with such a purely gaseous phase approach is illustrated. In the figure, a substantial duplication exists in terms of structural components when compared with FIG. 1. Accordingly, those components of the apparatus 12 described in FIG. 1 which reappear in FIG. 11 are identified by the same numeration in combination with a double prime. In the embodiment, cooling gas such as helium is introduced into the chamber 72" of target carriage 26" through stationary conduit 68". For this purpose, the end of conduit 68" within chamber 72" is coupled with a rotating seal 220. From this seal 220, there extend distribution conduits, two of which are seen at 222 and 224. These conduits as at 222 and 224 are coupled in gas transfer relationship between the seal and coupling 220, and a porous annular heat exchanger 226. Heat exchanger 226 is affixed to the upper wall of cardage 26" in heat exchange relationship therewith immediately beneath the target region 116". Formed of aluminum to permit neutron transfer therethrough and having a bottom outlet surface 228 spaced from the bottom surface or floor of chamber 72", the heat exchanger 226 serves as one component of a gas recirculation system wherein hot coolant gas, having experienced thermal exchange therein returns as represented by arrows 230 through the passageway intermediate conduits 78' and 66' for entry through conduits 80" and 84" to a gas cooling facility represented in general at block 232. A fan as at 234 symbolically represents a heat exchange at the facility 232. A cooling gas such as hydrogen, upon being cooled at facility 232, then returns to the target via conduits 90", valve 92", and conduit 68" for redistribution to the porous annular heat exchanger 226. The latter exchanger 226 may take on a variety of configurations, being formed of a labyrinth of bores or alternately being formed of a porous, sponge-like aluminum structure.

Where deuterium oxide is employed as a coolant within the chamber of target carriage 26, it is desirable to employ a highly pure form thereof. Accordingly, losses which may be encountered within the cooling condensing components of such a cooling arrangement may become excessive. Turning to FIG. 12, a cooling approach which utilizes the deuterium oxide as the coolant within a primary coolant chamber adjacent the target 116 region and a secondary chamber utilizing light water as a secondary coolant is illustrated. As before, in view of substantial commonality between the instant figure and FIG. 1 with respect to non-coolant features, those common components between the figures are represented in FIG. 12 in triple primed fashion.

Looking to the target carriage 26''', it may be observed that deuterium liquid is retained by centrifugal force at the region of target 116''' as shown at 240. This heavy water is retained within a primary coolant chamber represented generally at 242. The chamber 242 is shaped in annular fashion, the inward wall thereof being provided as a heat exchanger 244. Heat exchanger 244, while defining chamber 242 with the outer walls of the carriage 26''' preferably is formed having heat exchange fins or the like to increase surface area and provides for the condensing of vapor phase deuterium oxide to return that phase to a liquid phase in a self-contained reflux boiler or condenser configuration. Inwardly of the heat exchanger 244 is a secondary coolant chamber 246 which carries a light water coolant, the liquid phase of which is built up as at 248 as represented by arrows 250, the vapor phase of light water 248 exits through the gap intermediate conduit 68''' and 66''' to be directed via conduit 84''' to exhaust to atmosphere or for purposes of condensation depending upon the desires of the designer. Return or make-up light water is provided from along conduit 90''' under the control of valve 92''' to exit from the earlier-described end 70''' of stationary conduit 68'''. With the arrangement shown, the secondary, light water coolant is circulated throughout the more complex and thusly prone components of the system, while the heavy water primary coolant is confined and ideally localized at the vicinity of target region 116'''.

Figure 13:
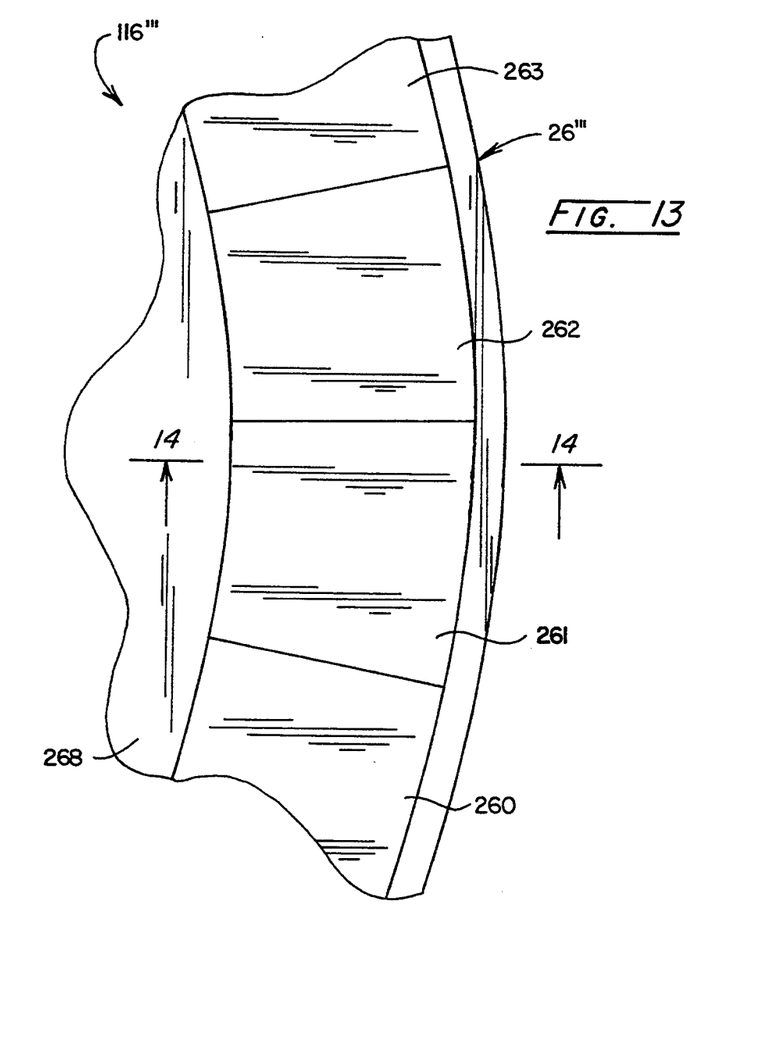
FIG. 13 is a partial top view of a target carriage and target region showing a target material encapsulation embodiment of the invention.
Figure 14:
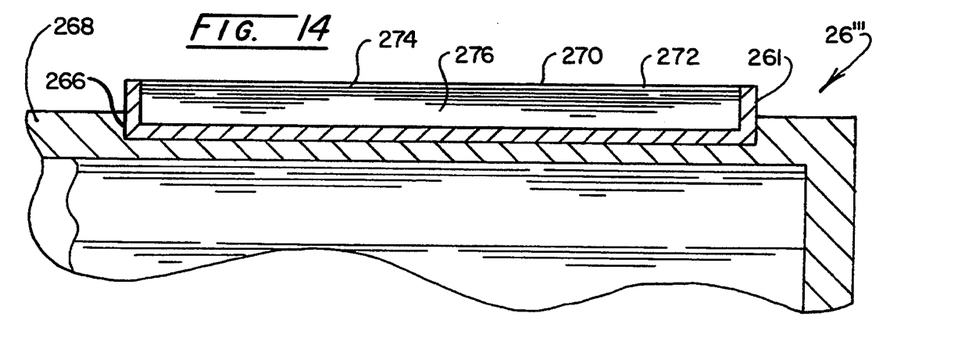
FIG. 14 is a sectional view taken through the plane 14—14 in FIG. 13.

Referring to FIGS. 13 and 14, a desirable alternative or addition to the capillary or surface tension based approach to retention of molten lithium metal at the target region 116 is illustrated. With this arrangement, discrete capsules 260–263 configured collectively for one embodiment to resemble an upwardly facing ring are fabricated. These capsules, having somewhat rectangular looking profiles are structured as containers for retaining lithium. The containers themselves, when filled with lithium metal, are covered with a thin window material which exhibits as low an atomic number as possible. For example, aluminum or beryllium foil may be used for this purpose. The foil, when aluminum, will be on the order of 10–25 microns in maximum thickness. Where beryllium is employed, a thickness of less than about 50 microns is provided. As an alternative, a vapor deposition at 1–2 microns in thickness may be considered. Looking to FIG. 13, a sequence of capsules as above described is represented within an portion of the outer periphery of target carriage Of the above sequence, capsule 261 is seen in sectional view in FIG. 14. Note that the capsule is mounted within an annular slot 266 formed within the upper aluminum plate surface 268 of carriage 26'. Mounting of the capsule for this purpose should be so as to provide for efficient heat transfer to the coolant system of the carriage 26 as described above in multiple embodiments. A foil cover for capsule 261 is shown at 270 spaced a predetermined gap 272 above the top surface 274 of the lithium target metal 276 to allow for volumetric thermal expansion of lithium. Generally, the lithium 276 contained within capsules as at 261 will have a thickness of about 0.040 inch or 0.100 cm. The gap 272 preferably is on the order of 0.002 cm to 0.005 cm in extent. In general, the aluminum foil 268 is soldered, or otherwise hermetically bonded to the upwardly disposed periphery of each capsule. Analysis of required Surface area for the target material shows that the capsules as at 260–263 also can be made having peripheral geometric shapes which are regular rectangles. Generally, the wall members which extend between the units would be maintained at a small thickness on the order of 0.10 to 0.05 inch. For example, for such structuring, the amount of target material lost to wall thickness is on the order of about 5% which is comparable or represents an improvement over the interstitial approaches described above.

Figure 15:
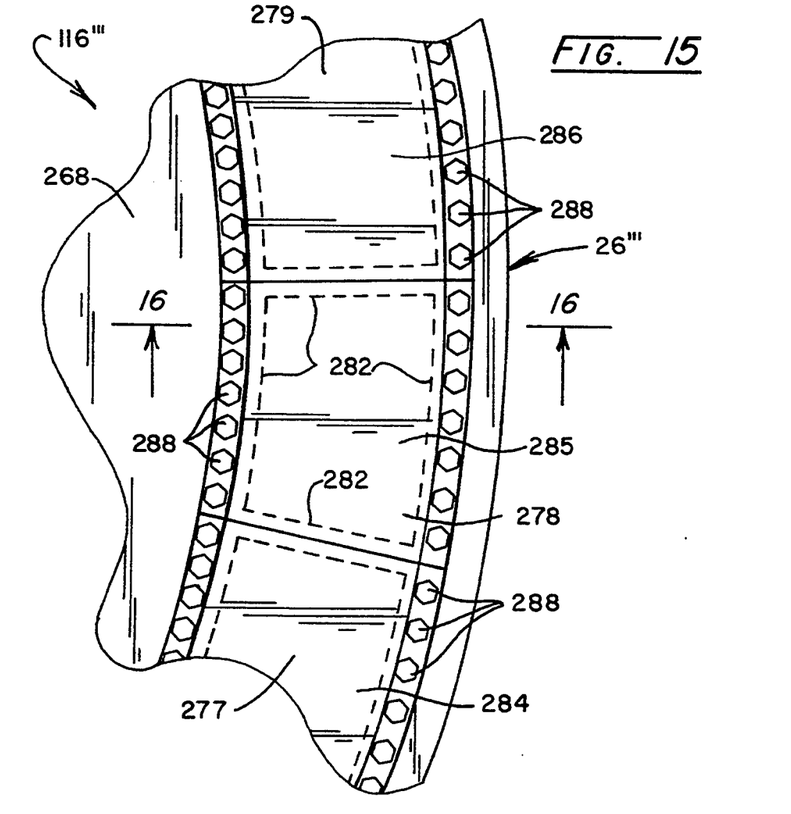
FIG. 15 is a partial top view of the target carriage and target region showing another target material encapsulation embodiment of the invention.
Figure 16:
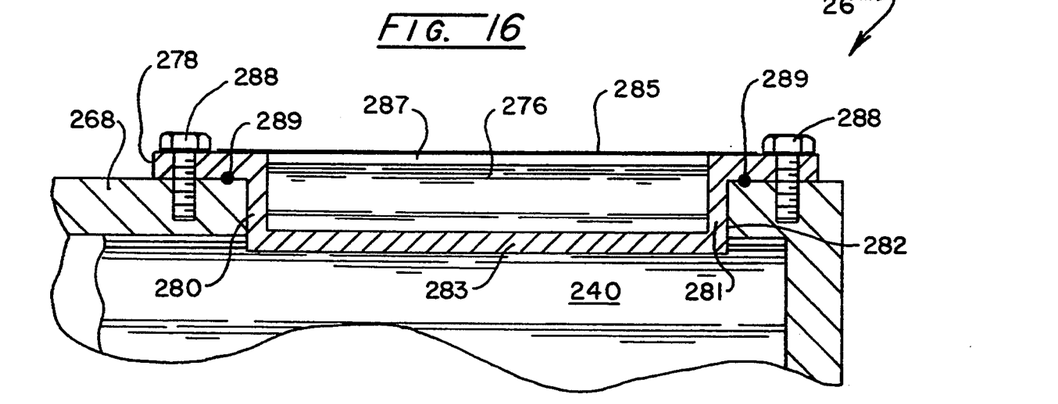
FIG. 16 is a sectional view taken through the plane 16—16 in FIG. 15.

Another embodiment of the capsule approach for retaining target materials at the upper plate surfaces such as at 268 is revealed in connection with FIGS. 15 and 16. Referring to FIG. 15, it may be seen that an arrangement of peripherally disposed discrete capsules is provided, three of which are represented in the sequence 277–279. As before, the sequence of capsules are configured such that they resemble an upwardly facing ring. Having somewhat rectangular looking profiles as before, the discrete capsules 277–279, as seen in FIG. 16, are configured as containers for retaining a target material such as lithium again identified at 276. In this regard, it may be observed in FIG. 16 that capsule 278 is configured having edge surfaces as at 280 and 281 which fit within openings as represented by the edge surface or periphery 282 which extend entirely through the plate upper surface 268 such that the bottom surface or base 283 of each capsule is in direct contact with deuterium oxide ($D_2O$) 240. This arrangement eliminates the thermal impedance and associated temperature difference which otherwise occurs at the interface, for example, between capsule 261 and upper plate surface 268 of the embodiment represented in connection with FIGS. 13 and 14.

As before, as seen in FIG. 16, each of the capsules 277–279 is provided with a foil cover as seen, respectively, at 284–286. As seen in FIG. 16, the cover, as before, is positioned to define a predetermined gap as at 287 extending above the upper surface of the lithium target material again represented at 276. The capsules as at 277–279 are retained by machine screws as at 288 and the coolant cavity beneath them is secured by such coupling when employed in conjunction with an O-ring seal as seen in FIG. 16 at 289.

The architecture thus developed also eliminates a need to form a high thermal conductance joint as by soldering or brazing as required in the embodiment of FIGS. 13 and 14 between, for example, the capsule 261 and upper plate surface 268. The elimination of a need for this bond also facilitates the removal and replacement of one or more of the target capsules 277–279 as may be required in the event of defective hermetic seals or refurbishment of target material, for example lithium, following extended use. As noted above, this use occurs with the bombardment of the lithium by ions which results in a conversion to a new element, for example, beryllium in the case of a lithium target material. The O-rings as at 289 may be formed using elastomeric or metallic materials. In the former regard, materials sold under the trademark "VITON" may be utilized (a trademark of E.I. dupont de nemours & Co.). Alternately, a flat gasket may be substituted for O-rings as at 289.

As noted earlier, a signficant benefit results from the utlization of capsulized target components as at 260–263 (FIGS. 13, 14) or as at 277–279 (FIGS. 15, 16). The capsules can be assembled under vacuum such that they may be maintained under normal ambient conditions for storage and maintenance purposes. Thus formed under vacuum, when the capsules are mounted within the vacuum containment chamber 28, the forces on either side of the foil as at 270 or 285 will be equalized, vacuum being positioned on either side. Likewise, when the capsules are exposed to normal atmospheric pressures, the forces on the foils as at 270 or 285 will be supported by the (solid) lithium layer 276 in close proximity to the foils 270 or 285. As the target is being employed and the lithium metal reaches a liquid phase, the only outward pressure upon foil 270 will be vapor pressure of the lithium component.

Figure 17:
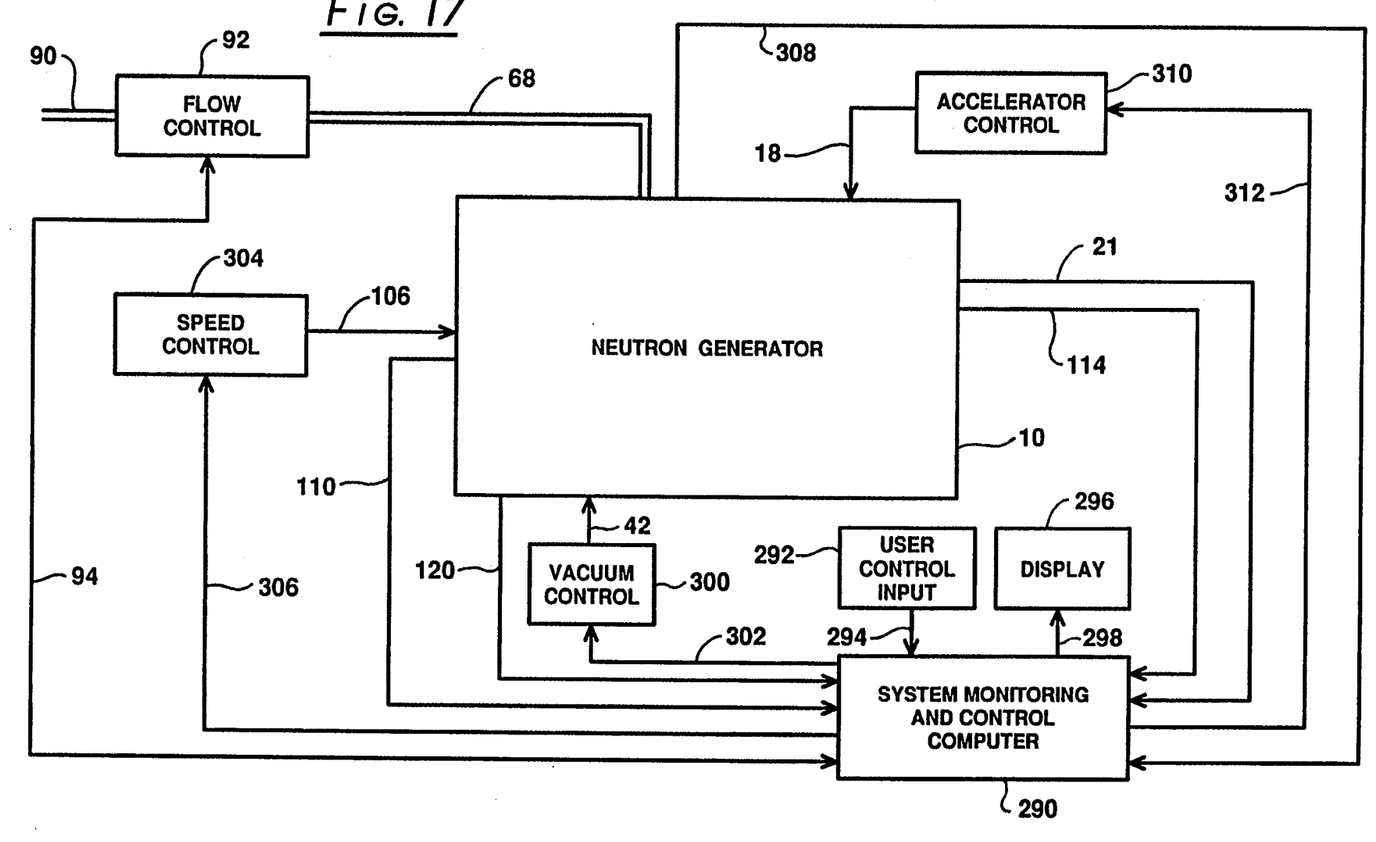
FIG. 17 is a block schematic diagram of a control and monitoring system employed with the apparatus of FIG. 1.

Referring to FIG. 17, a block diagrammatic representation of a control system for operating the neutron generator apparatus 10 is revealed. In the figure, the neutron generator apparatus as well as the earlier-described control inputs or signal outputs are identified with the same numeration as provided in conjunction with FIG. 1. In general, the monitoring and control is coordinated by a computer based control represented at block 290. In conventional fashion, user inputs are provided to this control as represented at block 292 and arrow 294. To facilitate this control, a display as represented at block 296 is driven from the control 290 as represented at line 298. While the monitoring and control 290 functions to maintain the operation of the apparatus 10 within predetermined operating limits, it also functions to carry out a predetermined sequence of operations or component actuations during start-up and shut-down of the system. For example, one sequence which might be selected for start-up resides initially in the activation of the vacuum control represented at block 300 by appropriate signaling from the control 290 via line 302. The vacuum control actuates pump 36 as earlier represented at line 42. As the vacuum pump 36 (FIG. 1) is controllably driven, the vacuum level within containment chamber 28 is monitored as at monitor 112 (FIG. 1 ). As described in the latter figure and reproduced in the instant figure, the monitoring signal output from monitor 112 is directed via line 114 to the control components 290. Where the vacuum level within containment chamber 28 reaches acceptable limits, the control components 290 commences the rotation of target carriage 26 through the activation of a speed control represented at block 304 through actuation thereof from line 306. Control power input then is directed to the motor assemblage 98 as represented at earlier-described line 106 which appears in the instant figure. The speed of rotation of the system via the shaft 104 motor assemblage 98 is monitored by tachometer 108 (FIG. 1 ) and the speed signal resulting therefrom is directed via earlier-described line 110 to the control components 290. Line 110 reappears in FIG. 15 being directed from the apparatus 10 to block 290.

As the rotational speed of target carriage 26 reaches a pre-selected level, a working fluid control as represented at block 92 will be actuated from the control components 290 as represented by line 94. Fluid input to the control 308, for example a water input, is represented at conduit 90. Control flow output then is directed to the cavity 72 of the target carriage 26 via stationary conduit 68. Components 90, 92, 94, and 68 have been described earlier in conjunction with FIG. 1 and reappear in the instant figure with that same numerical identification. The level of water within the chamber 72 of target carriage 26 and monitored at flow level sensor 142 has been described earlier as being combined with cabling at 94. For the instant illustration, that signal is shown being directed to control components 290 via line 308. As a fluid liquid volume is developed within the chamber 72 (FIG. 1) an appropriate signal is received along line 308 by control components 290 and the flow of coolant is adjusted accordingly at block 92.

After the operating conditions as above discussed are maintained within pre-selected limits for a predetermined period of time, the monitoring and control components 290 transmit a control signal to the accelerator control represented at block 310 via line 312 which is then transmitted along with power supplies and the like from cabling 18 to the accelerator 16 within the apparatus 10. Cabling 18 is represented in the instant figure by the same numeration used in conjunction with FIG. 1.

The accelerator control 310 provides for the commencement of the generation of protons or ions and increases the accelerator proton or ion beam current until it is within preselected limits based upon the continuous sampling signals transmitted from the beam current monitor 20 as conveyed via line 21. Line 21 reappears from FIG. 1 in the instant figure. As the system then generates neutrons, all controls are monitored, including the temperature control from temperature sensor 118. That sensor provides signals from along earlier-described line 120 which reappears in the instant figure as being directed to the control components at block 290.

If any of the monitored and control operating conditions exceed pre-selected limits, then a safe shut-down procedure automatically is initiated in which the accelerator and associated proton or ion beam current is shut down first, followed by a shut-down of the flow of working fluid within the coolant system, once the temperature sensed at monitor 118 falls below a pre-selected limit. A similar shut-down procedure will be followed at the completion of normal operation at the end of any neutron therapy.

Since certain changes may be made in the above-described system and apparatus without departing from the scope of the invention herein involved, it is intended that all matter contained in the above description or shown in the accompanying drawings shall be interpreted as illustrative and not in a limiting sense.

I claim:
1. Apparatus for generating neutrons, comprising:
   a particle source having an output of charged particles directed along a predetermined pathway
   a containment chamber for receiving said output of charged particles under subatmospheric pressure;
   a target carriage extending to a circular periphery, mounted for rotation about a carriage axis within said containment chamber, having a target support region extending inwardly from said periphery and movable across said pathway and having an internally disposed, confined coolant chamber extending into adjacency with said target support region, said coolant chamber including an annular heat exchanger positioned adjacent to and inwardly from said target support region defining a sealed primary coolant chamber extending beneath said target support region and retaining a deuterium oxide coolant in heat exchange relationship with th radially outwardly disposed surface of said annular heat exchanger, the radially inwardly disposed surface of said annular heat exchanger defining a second coolant chamber;
   a circulation conduit assembly having one end in fluid sealed connection with said target carriage secondary coolant chamber and extending outwardly from said containment chamber to a port assembly;
   a target assembly retaining neutron deriving target material, located at said target support region and reactive with said charged particles within said pathway to generate neutrons and heat; and
   a fluid coolant for circulation to said secondary coolant chamber through said circulation conduit assembly.

2. The apparatus of claim 1 in which said fluid coolant is $H_2O$.

3. The apparatus of claim 1 in which said target assembly comprises a plurality of capsules removably mountable upon said target carriage at said target support region, each said capsule being formed having a cavity within which said neutron deriving target material is retained, each said cavity having a lower disposed base extending through said target support region for direct, heat exchange association with said deuterium oxide coolant; and each said cavity being sealingly covered by a thin overlay material having a thickness and atomic number selected to permit substantial passage of said charged particles therethrough.

4. The apparatus of claim 3 in which said overlay material is a foil mounted above said target material a predetermined distance to define a gap dimensioned to accommodate a thermally induced expansion of said target material.

5. The apparatus of claim 3 in which said overlay material is aluminum having a thickness of less than about 25 microns.

6. The apparatus of claim 3 in which said overlay material is beryllium having a thickness of less than about 50 microns.

7. Apparatus for generating neutrons, comprising:
   a particle source having an output of charged particles directed along a predetermined pathway;
   a target carriage mounted for rotation about a carriage axis, having an outer periphery, and a target support region extending inwardly from said periphery;
   a target assembly including a plurality of capsules mountable upon said target carriage at said target support region, each said capsule being formed having a cavity within which a meltable neutron deriving target material is disposed, each said cavity being sealingly covered by a thin material overlay having a thickness and atomic number selected to permit substantial passage of said charged particles therethrough for impingement upon said target material to effect neutron generation; and
   a cooling assembly for removing heat generated at said target support region by said charged particle impingement.

8. The apparatus of claim 7 in which said overlay material is aluminum having a thickness of less than about 25 microns.

9. The apparatus of claim 8 in which said aluminum overlay is a foil mounted over each said capsule and spaced above said target material a predetermined distance to define a gap dimensioned to accommodate a thermally induced expansion of said target material.

10. The apparatus of claim 8 in which said capsule gap is at subatmospheric pressure.

11. The apparatus of claim 7 in which said overlay material is beryllium having a thickness of less than about 50 microns.

12. The apparatus of claim 21 in which:
   said cooling assembly includes a coolant chamber configured within said target carriage to retain a deuterium oxide coolant in heat exchange relationship with said target assembly at said target support region; and said target assembly capsules are removably mounted upon said target carriage, each said capsule cavity having a lower disposed base extending through said target support region for direct, heat exchange association with said coolant.

13. The apparatus of claim 12 in which said overlay material is a foil mounted above said target material a predetermined distance to define a gap dimensioned to accommodate a thermally induced expansion of said target material.

14. The apparatus of claim 12 in which said overlay material is aluminum having a thickness of less than about 25 microns.

15. The apparatus of claim 12 in which said overlay material is beryllium having a thickness of less than about 50 microns.

* * * * *